US012673018B2

(12) United States Patent
Yoshimura et al.

(10) Patent No.: US 12,673,018 B2
(45) Date of Patent: Jul. 7, 2026

(54) HYALURONATE SKIN-PENETRATING COSMETIC

(71) Applicant: SHISEIDO COMPANY, LTD., Tokyo (JP)

(72) Inventors: Mika Yoshimura, Tokyo (JP); Anna Okishima, Tokyo (JP); Takashi Oka, Tokyo (JP); Hiroko Shimizu, Tokyo (JP)

(73) Assignee: Shiseido Company, Ltd., Tokyo (JP)

( * ) Notice: Subject to any disclaimer, the term of this patent is extended or adjusted under 35 U.S.C. 154(b) by 258 days.

(21) Appl. No.: 18/559,989

(22) PCT Filed: May 30, 2022

(86) PCT No.: PCT/JP2022/022004

§ 371 (c)(1),
(2) Date: Nov. 9, 2023

(87) PCT Pub. No.: WO2022/259901

PCT Pub. Date: Dec. 15, 2022

(65) Prior Publication Data

US 2025/0032392 A1 Jan. 30, 2025

(30) Foreign Application Priority Data

Jun. 11, 2021 (JP) ................................. 2021-098315

(51) Int. Cl.
*A61K 8/73* (2006.01)
*A61Q 19/00* (2006.01)

(52) U.S. Cl.
CPC ............ *A61K 8/735* (2013.01); *A61Q 19/007* (2013.01); *A61K 2800/5428* (2013.01)

(58) Field of Classification Search
CPC .. A61K 8/735; A61K 2800/5428; A61K 8/20; A61K 8/44; A61K 8/73; A61Q 19/007; A61Q 19/00; A61Q 19/08
See application file for complete search history.

(56) References Cited

U.S. PATENT DOCUMENTS

| | | | |
|---|---|---|---|
| 2016/0151283 A1 | 6/2016 | Manca et al. | |
| 2016/0256379 A1 | 9/2016 | Stangl et al. | |

FOREIGN PATENT DOCUMENTS

| | | |
|---|---|---|
| CN | 108785141 A | 11/2018 |
| CN | 109172506 A | 1/2019 |
| CN | 112494412 A | 3/2021 |
| EP | 0 474 270 A1 | 3/1992 |
| JP | 2010-150151 A | 7/2010 |
| JP | 2012-082177 A | 4/2012 |
| JP | 2013-181001 A | 9/2013 |
| JP | 2016-222612 A | 12/2016 |
| WO | WO-2018/182003 A1 | 10/2018 |

*Primary Examiner* — Robert A Wax
*Assistant Examiner* — Kimberly Barber
(74) *Attorney, Agent, or Firm* — Foley & Lardner LLP

(57) ABSTRACT

To provide a hyaluronate skin-penetrating cosmetic that allows a hyaluronate to penetrate into the skin without a complicated step such as composite formation of a hyaluronate.
A hyaluronate skin-penetrating cosmetic of the present disclosure contains a hyaluronate and an amphoteric surfactant.

9 Claims, 6 Drawing Sheets

HYALURONATE SKIN-PENETRATING COSMETIC

CROSS-REFERENCE TO RELATED APPLICATIONS

This application is the U.S. National Stage of PCT/JP2022/022004, filed May 30, 2022, which claims priority to JP 2021-098315, filed Jun. 11, 2021.

FIELD

The present disclosure relates to a hyaluronate skin-penetrating cosmetic.

BACKGROUND

In the fields of cosmetics and the like, hyaluronates having a moisturizing function are utilized for the purpose of, for example, skin moisturization.

PTL 1 discloses a cosmetic containing hyaluronic acid-supported nanoparticles in which hyaluronic acid is supported at least inside or on the surfaces of nanoparticles formed of polylactic acid, polyglycolic acid, or a lactic acid-glycolic acid copolymer.

PTL 2 discloses a skin external preparation containing composite nanoparticles that contain (A) hyaluronic acid and (B) a zwitterionic compound, and have a particle size of 100 nm or less.

CITATION LIST

Patent Literature

[PTL 1] Japanese Unexamined Patent Publication (Kokai) No. 2010-150151
[PTL 2] WO 2018/182003

SUMMARY

Technical Problem

For example, the stratum corneum located in the outermost layer of the skin has a barrier function to prevent the entry of foreign substances into the skin from the outside world, and thus exhibits a property of hardly allowing an active ingredient applied to the skin to penetrate into the skin. Therefore, when a hyaluronic acid component such as a hyaluronate is simply applied to the skin, the moisturizing effect of the hyaluronic acid component is likely to remain on the surface of the skin, and only a short-term moisturizing effect can be exerted. As a result, for the improvement of skin wrinkles and the like, it is necessary to continue to frequently apply the hyaluronic acid component over an extended period.

In the technologies disclosed in PTLs 1 and 2, it is indispensable to perform nanoparticulation of hyaluronic acid by supporting hyaluronic acid on a support material such as polylactic acid, or by forming a composite of hyaluronic acid and other material (polyion complex formation), and both of these technologies require complicated steps such as ultracentrifugation for the production of a cosmetic.

In view of the above, a main object of the present disclosure is to provide a hyaluronate skin-penetrating cosmetic that allows a hyaluronate to penetrate into the skin without a complicated step such as composite formation of a hyaluronic acid component.

Solution to Problem

<Aspect 1>
A hyaluronate skin-penetrating cosmetic, comprising a hyaluronate and an amphoteric surfactant.
<Aspect 2>
The cosmetic according to aspect 1, comprising a salt at a concentration giving an ionic strength of 0.05 or more.
<Aspect 3>
The cosmetic according to aspect 1 or 2, wherein the content of the amphoteric surfactant is 0.01% by mass or more with respect to a total amount of the cosmetic.
<Aspect 4>
The cosmetic according to any one of aspects 1 to 3, wherein the amphoteric surfactant is at least one selected from the group consisting of betaine-type amphoteric surfactants, amino acid-type amphoteric surfactants, sulfonic acid-type amphoteric surfactants, sulfate-type amphoteric surfactants, and lecithin.
<Aspect 5>
The cosmetic according to any one of aspects 2 to 4, comprising a salt at a concentration giving an ionic strength of 0.05 or more, wherein the salt is at least one selected from the group consisting of monovalent salts, divalent salts, and trivalent salts.
<Aspect 6>
The cosmetic according to any one of aspects 2 to 4, comprising a salt at a concentration giving an ionic strength of 0.05 or more,
wherein the salt is at least one selected from the group consisting of a sodium salt and a magnesium salt.
<Aspect 7>
The cosmetic according to aspect 6, wherein the sodium salt is sodium chloride, and the magnesium salt is magnesium chloride.
<Aspect 8>
The cosmetic according to any one of aspects 1 to 7, comprising at least one moisturizing agent selected from the group consisting of propylene glycol, dipropylene glycol, and PEG/PPG-17/4 dimethyl ether.
<Aspect 9>
The cosmetic according to aspect 8, comprising sodium chloride.

Advantageous Effects of Invention

According to the present disclosure, a hyaluronate skin-penetrating cosmetic that allows a hyaluronate to penetrate into the skin without a complicated step such as composite formation of a hyaluronic acid component can be provided.

3

Figure 4:
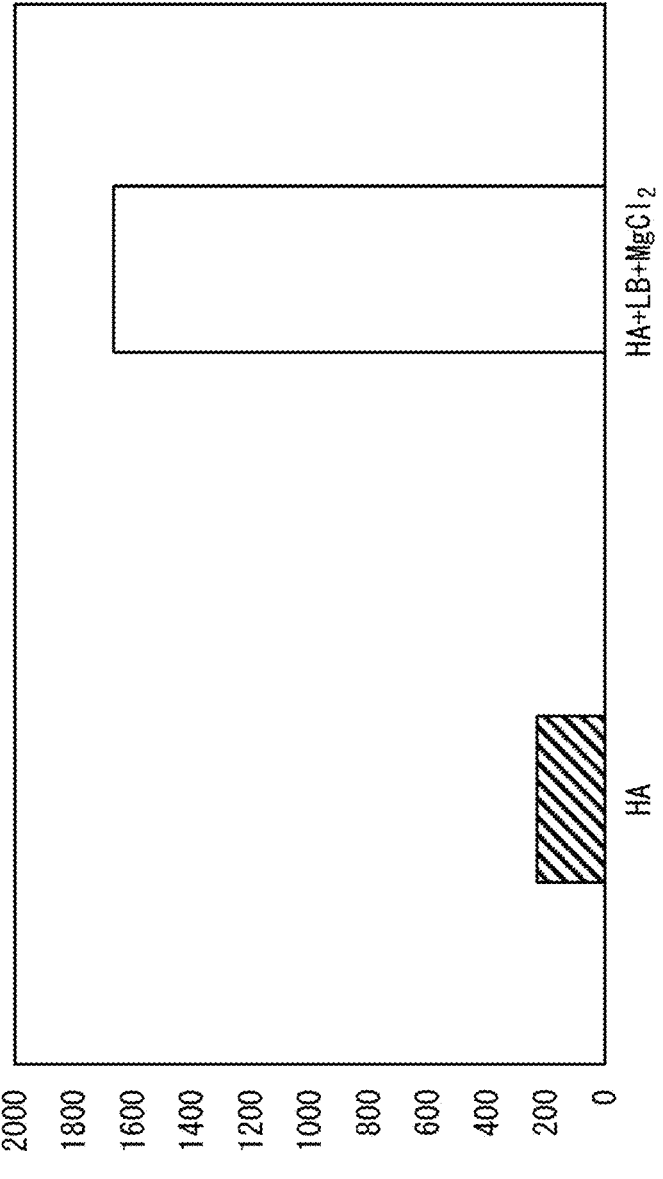

FIG. 4 is a graph related to the amount of a hyaluronate penetrated into a human skin in association with the incorporation of magnesium chloride, with the use of an amphoteric surfactant.

Figure 5:
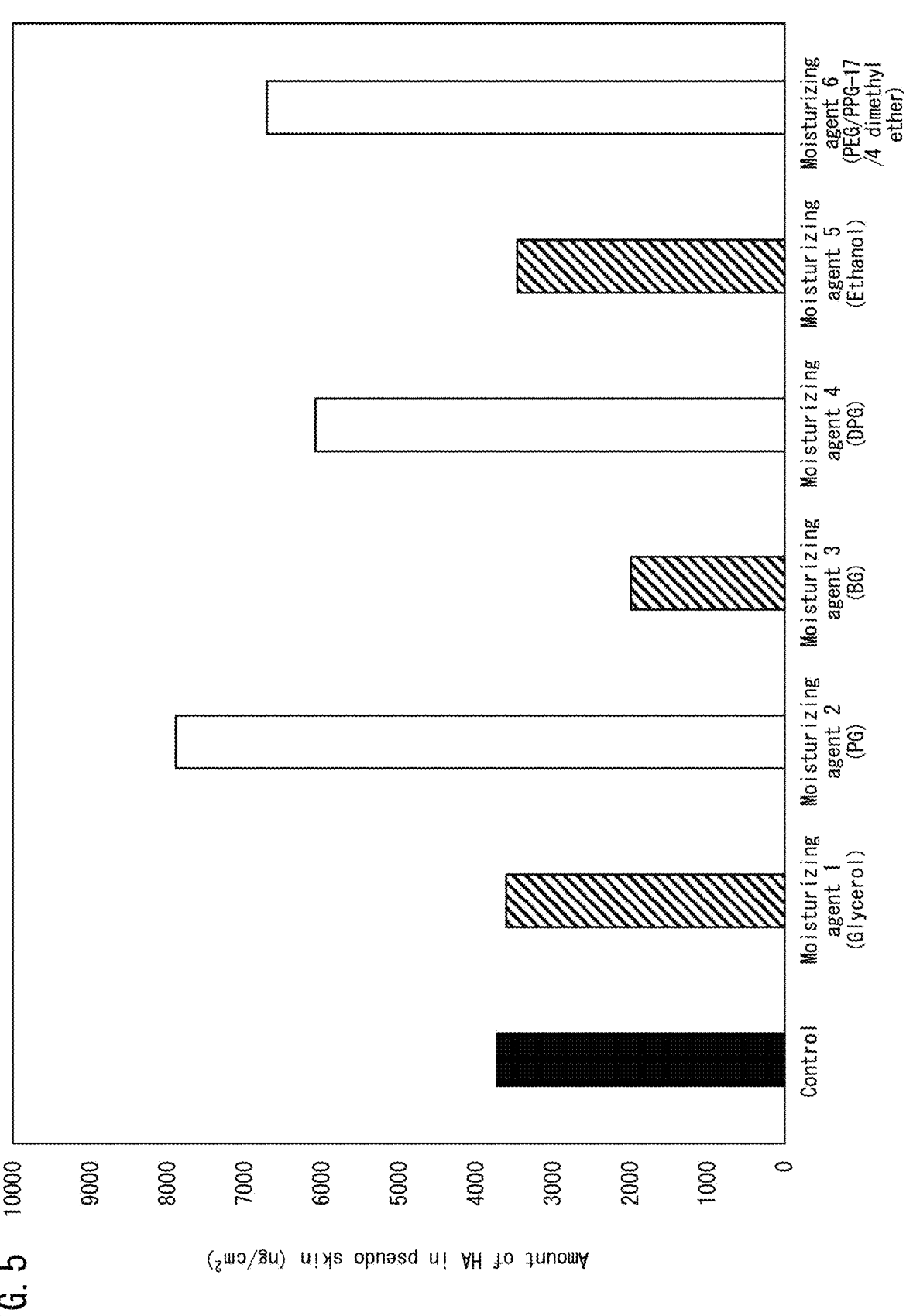

FIG. 5 is a graph related to the amount of a hyaluronate penetrated into a pseudo skin with the use of various moisturizing agents in combination with an amphoteric surfactant.

Figure 6:
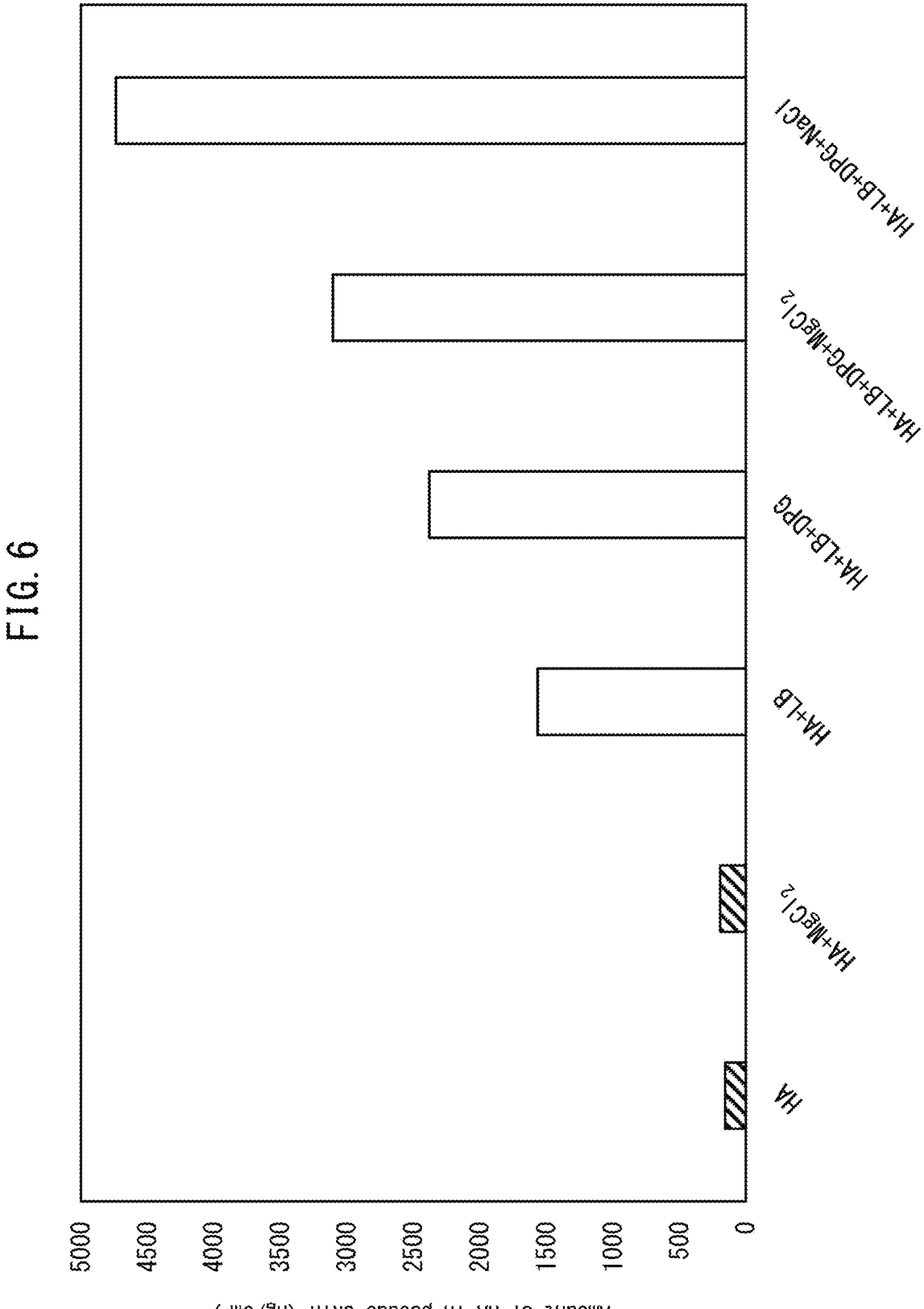

FIG. 6 is a graph related to the amount of a hyaluronate penetrated into a pseudo skin in association with the incorporation of sodium chloride or magnesium chloride, with the use of an amphoteric surfactant and a moisturizing agent (dipropylene glycol) in combination.

DESCRIPTION OF EMBODIMENTS

Embodiments of the present disclosure will now be described in detail. The present disclosure is, however, not limited to the below-described embodiments, and can be carried out with various modifications within the scope of the invention.

The hyaluronate skin-penetrating cosmetic of the present disclosure contains a hyaluronate and an amphoteric surfactant.

Without being bound by any principle, the action principle in which the cosmetic of the present disclosure facilitates the penetration of a hyaluronate into the skin by containing an amphoteric surfactant along with the hyaluronate is believed to be as follows.

Molecules of a hyaluronate typically have a high molecular weight and exist in a cosmetic in the state of being spread in a filamentous form. Therefore, even when a cosmetic containing a hyaluronate in such a state is applied to the skin, the molecules of the hyaluronate are likely to remain on the surface of the skin without penetrating into the skin.

The present inventors discovered that, by simply incorporating an amphoteric surfactant into a cosmetic along with a hyaluronate, penetration of the hyaluronate into the skin is facilitated even without nanoparticulation of the hyaluronate through a composite formation process such as ultracentrifugation as described in PTLs 1 and 2.

As for the reason why penetration of the hyaluronate into the skin is facilitated, it is believed that the amphoteric surfactant acts on, for example, the intercellular lipids of the skin. In other words, it is believed that the amphoteric surfactant is capable of forming micropores, microcracks, or the like in the intercellular lipids of the skin, as a result of which the hyaluronate is likely to penetrate into the skin through the pores or cracks. Further, in this process, it is believed that the positive charge of the amphoteric surfactant ionically binds with the negative charge of the hyaluronate in the vicinity of the skin to modify the polarity of the hyaluronate (apparently increase the hydrophobicity), whereby the hyaluronate is made likely to penetrate into the highly hydrophobic stratum corneum even without being nanoparticulated.

<<Skin-Penetrating Cosmetic>>

The cosmetic of the present disclosure contains a hyaluronate and an amphoteric surfactant, and has an effect of improving the penetration of the hyaluronate into the skin.

<Hyaluronate>

The hyaluronate that may be incorporated into the cosmetic of the present disclosure is not particularly limited. A "hyaluronate" generally refers to a salt of a linear polymer in which N-acetyl-D-glucosamine residues and D-glucuronic acid residues are alternately linked, and such a hyaluronate can be obtained by, for example, isolation-extraction from a cockscomb or other animal tissue, or fermentation using microbes belonging to the genus *Streptococcus* or the like.

As the hyaluronate, a metal salt of hyaluronic acid, such as sodium hyaluronate, potassium hyaluronate, magnesium hyaluronate, calcium hyaluronate, or aluminum hyaluronate can be used. A hyaluronate derivative obtained by etherification, esterification, amidation, acetylation, acetalization, or ketalization of a hydroxyl group, a carboxy group, or the like of hyaluronic acid can also be used as long as it contains a carboxyl group residue. The term "hyaluronate" used herein may encompass the concept of hyaluronates and derivatives thereof.

The weight-average molecular weight of the hyaluronate is not particularly limited and may be, for example, 10,000,000 or less. Not only hyaluronates but also low-molecular-weight agents are generally believed to readily infiltrate into the skin. An amphoteric surfactant can improve the penetration into the skin also for a low-molecular-weight hyaluronate; however, since a low-molecular-weight hyaluronate hardly stays inside the skin and thus has a poor water-retaining performance as compared to a high-molecular-weight hyaluronate, it may be difficult to maintain a moisture-retaining effect in the skin over an extended period. Therefore, in order to maintain a moisture-retaining effect in the skin over an extended period, it is advantageous to use a high-molecular-weight hyaluronate. From the viewpoint of the water-retaining performance inside the skin and the like, the weight-average molecular weight of the hyaluronate may be, for example, 500 or more, 1,000 or more, 5,000 or more, 10,000 or more, 50,000 or more, 100,000 or more, 300,000 or more, 500,000 or more, 800,000 or more, or 1,000,000 or more, and may be, for example, 10,000,000 or less, 8,000,000 or less, 5,000,000 or less, 3,000,000 or less, 2,000,000 or less, or 1,500,000 or less. The term "weight-average molecular weight" used herein refers to a weight-average molecular weight in terms of polystyrene that is determined by gel permeation chromatography.

As the hyaluronate, any of hyaluronates and derivatives thereof may be used singly, or two or more of hyaluronates and derivatives thereof may be used in combination. The hyaluronates and derivatives thereof to be used may have the same molecular weight, or different molecular weights.

As the hyaluronate, a commercially available product may be used as well. Examples of the commercially available hyaluronate include hyaluronic acid HA-LQ (manufactured by Kewpie Corporation), hyaluronic acid FCH (manufactured by Kikkoman Biochemifa Company), and sodium biohyaluronate HA12N (manufactured by Shiseido Co., Ltd.).

In some embodiments, the hyaluronate contained in the cosmetic of the present disclosure does not need to be made into composite nanoparticles as described in PTLs 1 and 2; therefore, in a hyaluronate-containing component allowed to penetrate into the skin, the content of the hyaluronate can be maintained at a high concentration.

However, in the hyaluronate-containing component allowed to penetrate into the skin, a polymer component other than the hyaluronate may be contained within a range that does not cause a problem in the moisturizing performance and the like. The content ratio of such other polymer component may be, for example, less than 50% by mass, 40% by mass or less, 30% by mass or less, 20% by mass or less, 10% by mass or less, 5% by mass or less, 3% by mass or less, or 1% by mass or less, with respect to a total amount of polymers contained in the hyaluronate-containing component. It is noted here that the content ratio of the hyaluronate in the hyaluronate-containing component can be determined by, for example, the ELISA method.

In some embodiments, the cosmetic of the present disclosure does not contain any composite nanoparticle that contains a hyaluronate and a zwitterionic compound and has a particle size of 100 nm or less.

From the viewpoint of moisture retention, cost, and the like, the amount of the hyaluronate contained in the cosmetic may be, for example, 0.005% by mass or more, 0.01% by mass or more, 0.05% by mass or more, 0.10% by mass or more, 0.15% by mass or more, 0.20% by mass or more, or 0.25% by mass or more, but 1.0% by mass or less, 0.80% by mass or less, 0.60% by mass or less, 0.50% by mass or less, or 0.45% by mass or less, with respect to a total amount of the cosmetic. The cosmetic of the present disclosure can provide a sufficient moisturizing effect even when the content of the hyaluronate therein is relatively low since, as described above, the content of the hyaluronate in the hyaluronate-containing component can be maintained at a high concentration and, at the same time, the amphoteric surfactant incorporated into the cosmetic allows the hyaluronate to penetrate into the skin in a preferred manner.

<Amphoteric Surfactant>

The cosmetic of the present disclosure contains an amphoteric surfactant in addition to the hyaluronate. An amphoteric surfactant may be used singly, or two or more kinds of amphoteric surfactants may be used in combination.

The amphoteric surfactant is not particularly limited and may be, for example, at least one selected from the group consisting of betaine-type amphoteric surfactants, amino acid-type amphoteric surfactants, sulfonic acid-type amphoteric surfactants, sulfate-type amphoteric surfactants, and lecithin. Thereamong, from the viewpoint of the penetration of the hyaluronate into the skin, betaine-type amphoteric surfactants and lecithin are preferred, and lecithin is particularly preferred. As the lecithin, hydrogenated lecithin may be used.

Examples of the betaine-type amphoteric surfactants include alkyl betaine-type amphoteric surfactants, amidobetaine-type amphoteric surfactants, imidazolinium betaine-type amphoteric surfactants, and sulfobetaine-type amphoteric surfactants. Examples of particularly preferred betaine-type amphoteric surfactants include lauryl betaine, imidazolinium betaine, and cocamidopropyl betaine.

Examples of the amino acid-type amphoteric surfactants include alkyl amino acids having an alkyl group having 6 to 18 carbon atoms. Specific examples thereof include N-lauryl-β-alanine, N-stearyl-β-alanine, lauryldiaminoethylglycine, and N-[3-alkyl(12,14)oxy-2-hydroxy propyl]-L-arginine hydrochloride.

Examples of the sulfonic acid-type amphoteric surfactants include alkylamino sulfonic acids and alkyl imidazoline sulfonic acids. Specific examples thereof include decyldimethyl aminopropyl sulfonic acid, lauryldimethyl aminopropyl sulfonic acid, palmityl dimethylpropyl sulfonic acid, lauryl di-n-propylaminopropyl sulfonic acid, and 2-undecylimidazoline-N-ethyl sulfonic acid.

Examples of the sulfate-type amphoteric surfactants include alkylamino sulfuric acids and alkyl imidazoline sulfuric acids. Specific examples thereof include decyldimethyl aminopropyl sulfuric acid, lauryldimethyl aminopropyl sulfuric acid, palmityldimethyl aminopropyl sulfuric acid, lauryl di-n-propylaminopropyl sulfuric acid, and 2-undecylimidazoline-N-ethyl sulfuric acid.

From the viewpoint of the penetration of the hyaluronate into the skin, the amount of the amphoteric surfactant to be incorporated may be, for example, 0.01% by mass or more, 0.03% by mass or more, 0.05% by mass or more, 0.07% by mass or more, 0.10% by mass or more, 0.13% by mass or more, 0.15% by mass or more, 0.17% by mass or more, or 0.20% by mass or more, but 5.0% by mass or less, 4.0% by mass or less, 3.0% by mass or less, or 2.0% by mass or less, with respect to a total amount of the cosmetic.

<Aqueous Medium>

The cosmetic of the present disclosure may typically contain an aqueous medium. The aqueous medium is not particularly limited, and any aqueous medium that is used in cosmetics, quasi-drugs, and the like may be used. Examples of such an aqueous medium include ion exchange water, distilled water, ultrapure water, tap water, and buffers. These aqueous media may be used singly, or in combination of two or more kinds thereof.

Examples of the buffers include a citrate buffer, a lactate buffer, a phosphate buffer, an acetate buffer, a tartrate buffer, a borate buffer, and a Tris buffer. From the viewpoint of ensuring a high buffer capacity, a citrate buffer, a lactate buffer, and a phosphate buffer are preferred, and a citrate buffer is more preferred.

The pH of the buffer may be 7.0 or less, 6.8 or less, or 6.5 or less. A lower limit value of the pH of the buffer is not particularly limited; however, for example, from the viewpoint of irritation to the skin, it is preferably 4.5 or more, 5.5 or more, or 6.0 or more.

<Optional Components>

In the cosmetic of the present disclosure, various components may be incorporated as appropriate within a range that does not adversely affect the effects of the present invention. Examples of such components include: salts; moisturizing agents; skin or hair nutrients; vitamins; water-soluble agents applicable to pharmaceuticals, quasi-drugs, cosmetics, and the like; ultraviolet absorbers; antioxidants; preservatives; antioxidant aids; thickeners; pigments; dyes; colorants; and fragrances. These optional components may be used singly, or in combination of two or more kinds thereof.

(Salt)

Figure 2:
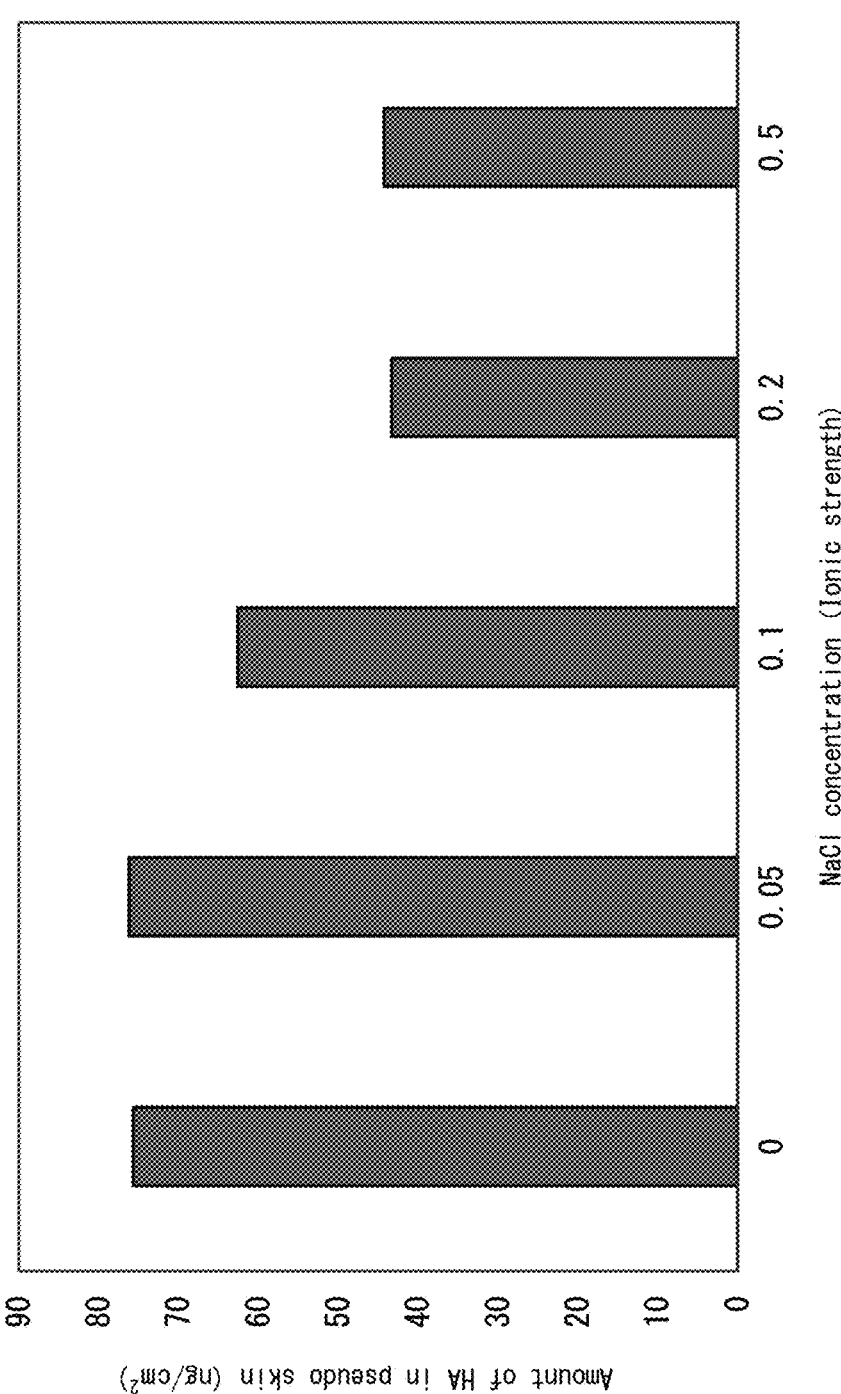
FIG. 2 is a graph related to the amount of a hyaluronate penetrated into a pseudo skin in association with the incorporation of sodium chloride, without the use of an amphoteric surfactant.
Figure 3:
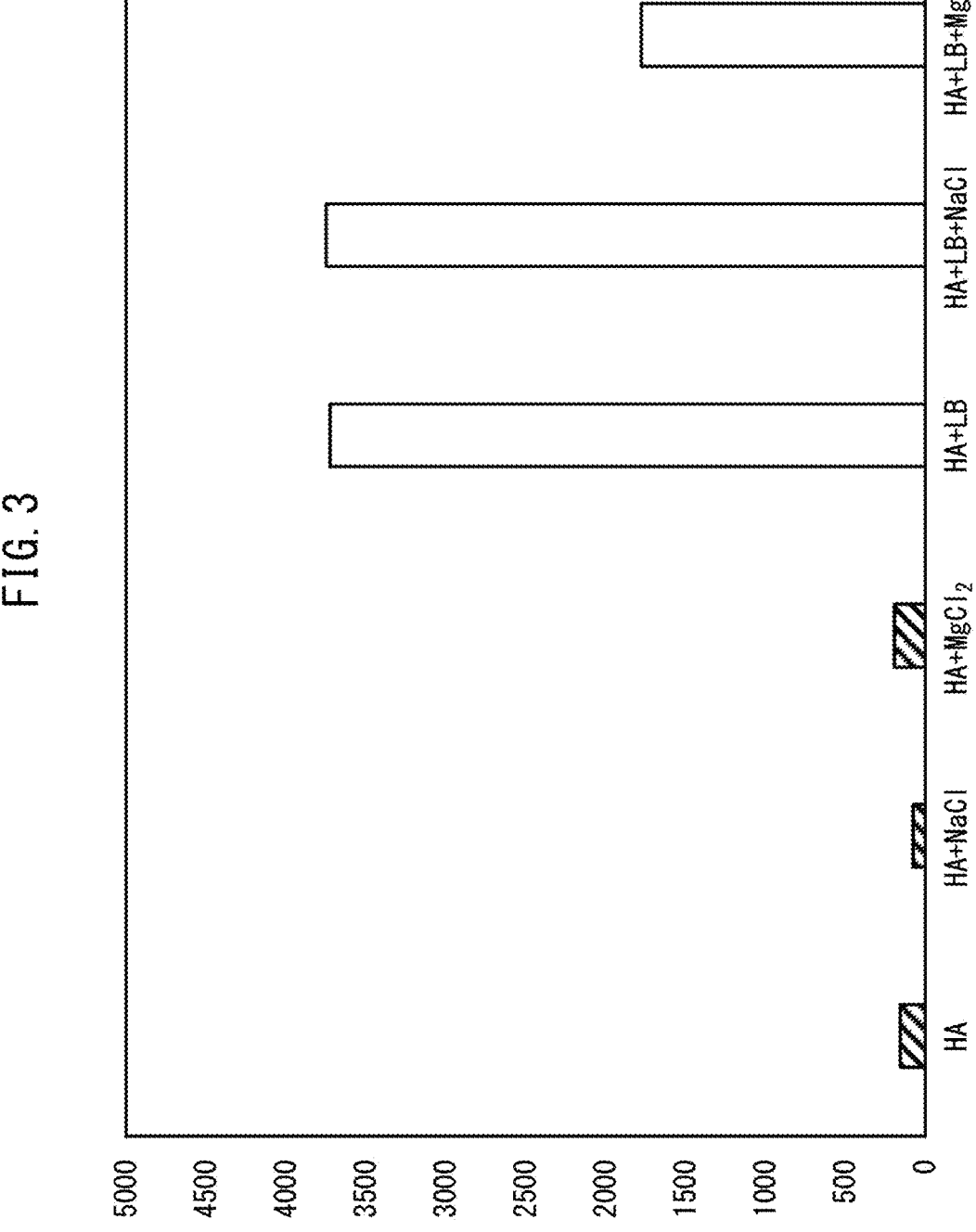
FIG. 3 is a graph related to the amount of a hyaluronate penetrated into a pseudo skin in association with the incorporation of sodium chloride or magnesium chloride, with the use of an amphoteric surfactant.

The cosmetic of the present disclosure may contain a salt. When a salt is contained in a hyaluronate-containing cosmetic, as depicted in FIG. 2, the amount of the hyaluronate (HA) penetrating into the skin may be reduced. However, since the cosmetic of the present disclosure contains an amphoteric surfactant along with a hyaluronate, the hyaluronate is allowed to penetrate into the skin in a favorable manner even when the cosmetic of the present disclosure contains a salt. A salt may be used singly, or two or more kinds of salts may be used in combination. It is noted here that the term "salt" used herein does not encompass hyaluronates.

The salt that may be incorporated into the cosmetic is not particularly limited and may be, for example, at least one salt selected from the group consisting of inorganic salts and organic acid salts. Considering the use as a cosmetic, among inorganic salts and organic acid salts, the salt is preferably one which hardly exerts an adverse effect on the skin. The term "inorganic salt" used herein refers to a salt consisting of only inorganic components, and may be paraphrased as "salt formed by ions generated from an inorganic acid and an inorganic base". Further, the term "organic acid salt" used herein refers to a salt formed by an organic acid and a metal ion that are bound to each other. It is noted here that, in the cosmetic, the salt generally exists in the form of an ion derived from the salt. Accordingly, in the present disclosure, for example, a "cosmetic containing a salt" indicates that the salt is contained in the form of such an ion. Further, the term "salt" used herein does not encompass ionic surfactants.

As the salt, for example, at least one selected from the group consisting of monovalent salts, divalent salts, and trivalent salts can be used.

As an inorganic salt, at least one selected from the group consisting of sodium salts, potassium salts, calcium salts, magnesium salts, and aluminum salts is preferred, and at least one selected from the group consisting of sodium salts and magnesium salts is more preferred.

Specific examples of the inorganic salt include sodium nitrate, sodium sulfate, sodium chloride, potassium nitrate, potassium sulfate, potassium chloride, calcium nitrate, calcium sulfate, calcium chloride, magnesium nitrate, magnesium sulfate, magnesium chloride, aluminum nitrate, aluminum sulfate, and aluminum chloride. Thereamong, sodium chloride and magnesium chloride are preferred, and sodium chloride is more preferred.

Specific examples of an organic acid salt include citrates, acetates, lactates, tartrates, succinates, malates, glycolates, salicylates, and pyrrolidone carboxylates. Specific examples of these organic acid salts include salts in which an organic acid such as citric acid, acetic acid, lactic acid, tartaric acid, succinic acid, malic acid, glycolic acid, salicylic acid, or pyrrolidone carboxylic acid is bound to a metal ion such as sodium ion, potassium ion, calcium ion, magnesium ion, or aluminum ion.

The cosmetic of the present disclosure can improve the penetration of the hyaluronate into the skin by containing the amphoteric surfactant: therefore, a salt can be incorporated into the cosmetic at a high concentration. The ionic strength of the salt in the cosmetic may be, for example, 0.05 or more, 0.06 or more, 0.07 or more, or 0.08 or more, but 5.0 or less, 4.0 or less, 3.0 or less, 2.0 or less, 1.0 or less, 0.7 or less, 0.5 or less, 0.4 or less, or 0.3 or less.

For example, when the cosmetic is prepared by adding a salt to a buffer, the ionic strength of the salt is calculated based on all salt components including a salt component(s) contained in the buffer itself and a salt component(s) separately added to the buffer.

(Moisturizing Agent)

The cosmetic of the present disclosure may contain a moisturizing agent. A moisturizing agent may be used singly, or two or more kinds of moisturizing agents may be used in combination. It is noted here that the term "moisturizing agent" used herein does not encompass hyaluronates.

Among moisturizing agents, at least one selected from the group consisting of propylene glycol, dipropylene glycol, and PEG/PPG-17/4 dimethyl ether is preferred. By using any of these moisturizing agents in combination with the hyaluronate and the amphoteric surfactant, the penetration of the hyaluronate into the skin can be further improved. Moreover, by using the aforementioned magnesium chloride and/or sodium chloride, particularly sodium chloride, in combination with any of these moisturizing agents, the hyaluronate, and the amphoteric surfactant, the penetration of the hyaluronate into the skin can be still further improved.

From the viewpoint of the penetration of the hyaluronate into the skin, the amount of the moisturizing agent to be incorporated into the cosmetic may be 1.0% by mass or more, 3.0% by mass or more, 5.0% by mass or more, or 7.0% by mass or more, but 30.0% by mass or less, 25.0% by mass or less, 20.0% by mass or less, or 15.0% by mass or less.

<Penetration of Cosmetic>

The penetration of the hyaluronate contained in the cosmetic of the present disclosure can be evaluated by, for example, the below-described penetration test 1 using a pseudo skin. In this penetration test, the cosmetic of the present disclosure can achieve a hyaluronate amount of 500 ng/cm$^2$ or more, 1,000 ng/cm$^2$ or more, or 1,500 ng/cm$^2$ or more, in the pseudo skin. An upper limit value of the hyaluronate amount is not particularly limited and may be, for example, 20,000 ng/cm$^2$ or less, 18,000 ng/cm$^2$ or less, 15,000 ng/cm$^2$ or less, or 12,000 ng/cm$^2$ or less.

<<Cosmetic Preparation Method>>

The cosmetic of the present disclosure can be prepared by, for example, the following method. As various materials to be used in the cosmetic preparation method such as hyaluronates, amphoteric surfactants, water, and optional components (e.g., salts and moisturizing agents), the above-described materials can be used.

The cosmetic can be prepared by adding an amphoteric surfactant and, as required, a salt and/or a moisturizing agent to water or a buffer, mixing these materials with stirring to prepare a solution, adding a hyaluronate to this solution, and then dissolving the hyaluronate while mixing the solution with stirring.

Alternatively, the cosmetic can be prepared by adding a hyaluronate to water or a buffer, dissolving the hyaluronate while mixing the resulting solution with stirring, subsequently adding an amphoteric surfactant and, as required, a salt and/or a moisturizing agent, and then mixing the resultant with stirring.

<<Application Site of Cosmetic>>

The cosmetic of the present disclosure is applicable to any part of the body, and may be applied to, for example, anywhere on the skin surface (body surface). Specifically, the cosmetic of the present disclosure can be applied as appropriate to, for example, the skin surface of the face (e.g., lips, eyes, eyelids, cheeks, forehead, glabella, and nose), head (scalp), ears, hands, arms, neck, legs, feet, chest, abdomen, back, and the like. It is noted here that the skin includes nails formed by alteration and hardening of the corneum of the skin epidermis.

In this manner, the cosmetic of the present disclosure can be suitably used as a hyaluronate skin-penetrating cosmetic.

<<Beauty Method Using Cosmetic>>

A beauty method using the cosmetic of the present disclosure includes applying the above-described cosmetic to the body surface. The term "beauty method" used herein refers to a method of adjusting the skin condition and making the skin beautiful by applying the cosmetic of the present disclosure to the body surface, which is different from a method of performing an operation, a treatment, or a diagnosis of a human.

Generally, the skin exposed to dryness is unknowingly deprived of moisture, leading to a state where the moisture content on the skin surface cannot be maintained. For example, when the moisture on the skin surface is insufficient, the moisturizing component produced by the skin itself (Natural Moisturizing Factor (NMF)) can no longer be successfully produced. Consequently, the barrier function and the moisturizing function on the skin surface are deteriorated, and the skin becomes more susceptible to damage, which is believed to result in the loss of moisture, causing wrinkles, skin roughness, and the like.

The cosmetic of the present disclosure allows its hyaluronate to penetrate into the skin in a preferred manner, and thus can favorably moisturize the skin. As a result, for example, not only the function of the skin itself to generate the moisturizing component but also poor turnover in the stratum corneum can be improved: therefore, troubles such as skin roughness are made less likely to occur, so that the beauty effect can be enhanced.

Means for using the cosmetic on the body surface is not particularly limited and, for example, the cosmetic can be applied to the body surface. As means for applying the cosmetic to the body surface, for example, the cosmetic may be sprayed on the skin using a spray container into which the cosmetic is put. Alternatively, the cosmetic may be put into a container that does not have a spray function, and an appropriate amount of the cosmetic may be collected on a finger, palm, or the like from the container and spread over the body surface.

EXAMPLES

The present invention will now be described in more detail by way of Test Examples and Examples; however, the present invention is not limited thereto. Hereinafter, unless otherwise specified, amounts are indicated in % by mass.

Test Examples 1 to 6

<Evaluation of Cosmetics>

Cosmetics obtained by the below-described respective production methods were each evaluated as described below, and the results thereof are summarized in Tables 1 to 6 and FIGS. 1 to 6. It is noted here that, in these Tables and FIGS., "HA", "LB", "PG", "BG", and "DPG" denote a hyaluronate, lauryl betaine, propylene glycol, butylene glycol, and dipropylene glycol, respectively.

(Penetration Test 1: Evaluation of Amount of Hyaluronate Penetrated into Pseudo Skin)

A STRAT-M (trademark) membrane (manufactured by Merck Millipore Ltd.) was used as a pseudo skin in a diffusion cell array system provided with a donor section and a receptor section (manufactured by Ikeda Scientific Co., Ltd.).

The STRAT-M (trademark) membrane was arranged between the donor section and the receptor section of the diffusion cell array system. In this process, the STRAT-M (trademark) membrane had an effective diffusion area of 0.785 cm$^2$. The receptor section was filled with 2 ml of a receptor liquid (PBS solution), and this receptor liquid was continuously stirred with a stirring bar. The surface temperature of the STRAT-M (trademark) membrane was set at 32° C., and each cosmetic was applied to the donor section in an amount of 10 μL/cm$^2$. After 24 hours, the STRAT-M (trademark) membrane was taken out, and the surface thereof was washed with an aqueous soap solution and purified water, after which the membrane was immersed in purified water and ultrasonically treated for 20 minutes. Further, extraction was performed overnight in a 37° C. thermostat bath, and a hyaluronate was quantified by the ELISA method. It is noted here that the values shown in Tables and FIGS. are each an average value of the hyaluronate amount measured three to four times. With regard to Reference Example 3 and Examples 12 to 14 of Test Example 6, the STRAT-M (trademark) membrane was taken out and the same operations were performed after 6 hours from the application of each cosmetic to the donor section in an amount of 10 μL/cm$^2$.

(Penetration Test 2: Evaluation of Amount of Hyaluronate Penetrated into Human Skin)

By a tape stripping method, the penetration of a hyaluronate was evaluated based on the amount of the hyaluronate recovered from the stratum corneum peeled off with a tape in accordance with the following procedures (1) to (7). It is noted here that this evaluation test was conducted for six panelists in their twenties, and the average values thereof are shown in Tables and FIGS.:

(1) A medial part of the forearm of each panelist was washed with soap;

(2) Each cosmetic was applied to the thus washed medial part of the forearm of each panelist at a rate of about 10 μl/cm$^2$;

(3) Each panelist was put on standby for 4 hours;

(4) The medial part of the forearm of each panelist was washed with purified water;

(5) The stratum corneum of the region to which the cosmetic was applied was tape-stripped ten times;

(6) The stratum corneum adhered to the tape was immersed in purified water, and a hyaluronate was extracted by ultrasonication; and (7) The resulting extract was analyzed by the ELISA method to quantify the hyaluronate in the extract.

Test Example 1: Various Surfactants

In Test Example 1, the effects of various surfactants blended with a hyaluronate were examined. The results thereof are shown in Tables 1 and 2 and FIG. 1. It is noted here that, in Tables 1 and 2 and FIG. 1, "nonionic activator", "amphoteric activator", and "anionic activator" refer to a nonionic surfactant, an amphoteric surfactant, and an anionic surfactant, respectively.

Comparative Example 1

A hyaluronate (manufactured by Shiseido Co., Ltd., BIOHYALURO 12: weight-average molecular weight=1,200,000) was added to ion-exchange water to a content of 0.3% by mass, and the resultant was mixed with stirring using a stirrer to prepare a hyaluronate-containing solution. To this solution, POE (20) behenyl ether which is a nonionic surfactant was added to a content of 0.7% by mass, and the resultant was mixed with stirring using a stirrer, whereby a test sample was prepared.

Comparative Examples 2 to 10 and Examples 1 to 5

Test samples of Comparative Examples 2 to 10 and Examples 1 to 5 were each prepared in the same manner as in Comparative Example 1, except that the surfactant was changed as shown in Tables 1 and 2.

Reference Example 1

As a test sample (control sample) of Reference Example 1, the hyaluronate-containing solution of Comparative Example 1 was used.

TABLE 1

| | Reference Example 1 | Comparative Example 1 | Comparative Example 2 | Comparative Example 3 | Comparative Example 4 Surfactant | Comparative Example 5 | Comparative Example 6 | Comparative Example 7 |
|---|---|---|---|---|---|---|---|---|
| | | | | | Nonionic activator | | | |
| | — | 1 | 2 | 3 | 4 | 5 | 6 | 7 |
| Penetration Test 1 (ng/cm²) | 155 | 600 | 270 | 340 | 1,270 | 350 | 410 | 420 |

Nonionic activator 1: POE (20) behenyl ether
Nonionic activator 2: POE (30) behenyl ether
Nonionic activator 3: PEG-60 glyceryl isostearate
Nonionic activator 4: PEG-20 glyceryl isostearate
Nonionic activator 5: POE (60) hardened castor oil
Nonionic activator 6: PPG-13 decyltetradeceth-24
Nonionic activator 7: PEG-2 laurate

TABLE 2

| | Example 1 | Example 2 | Example 3 | Example 4 | Example 5 Surfactant | Comparative Example 8 | Comparative Example 9 | Comparative Example 10 |
|---|---|---|---|---|---|---|---|---|
| | | Amphoteric activator | | | | | Anionic activator | |
| | 1 | 2 | 3 | 4 | 5 | 1 | 2 | 3 |
| Penetration Test 1 (ng/cm²) | 3,860 | 3,720 | 4,020 | 10,370 | 4,250 | 460 | 210 | 210 |

Amphoteric activator 1: cocamide amidopropyl betaine
Amphoteric activator 2: lauryl betaine
Amphoteric activator 3: myristyl sulfobetaine
Amphoteric activator 4: mixture of hydrogenated lecithin and ethanol
Amphoteric activator 5: imidazolinium betaine
Anionic activator 1: Na stearoyl glutamate
Anionic activator 2: Na methyl taurate
Anionic activator 3: Na methyl stearoyl taurate (Results)

Figure 1:
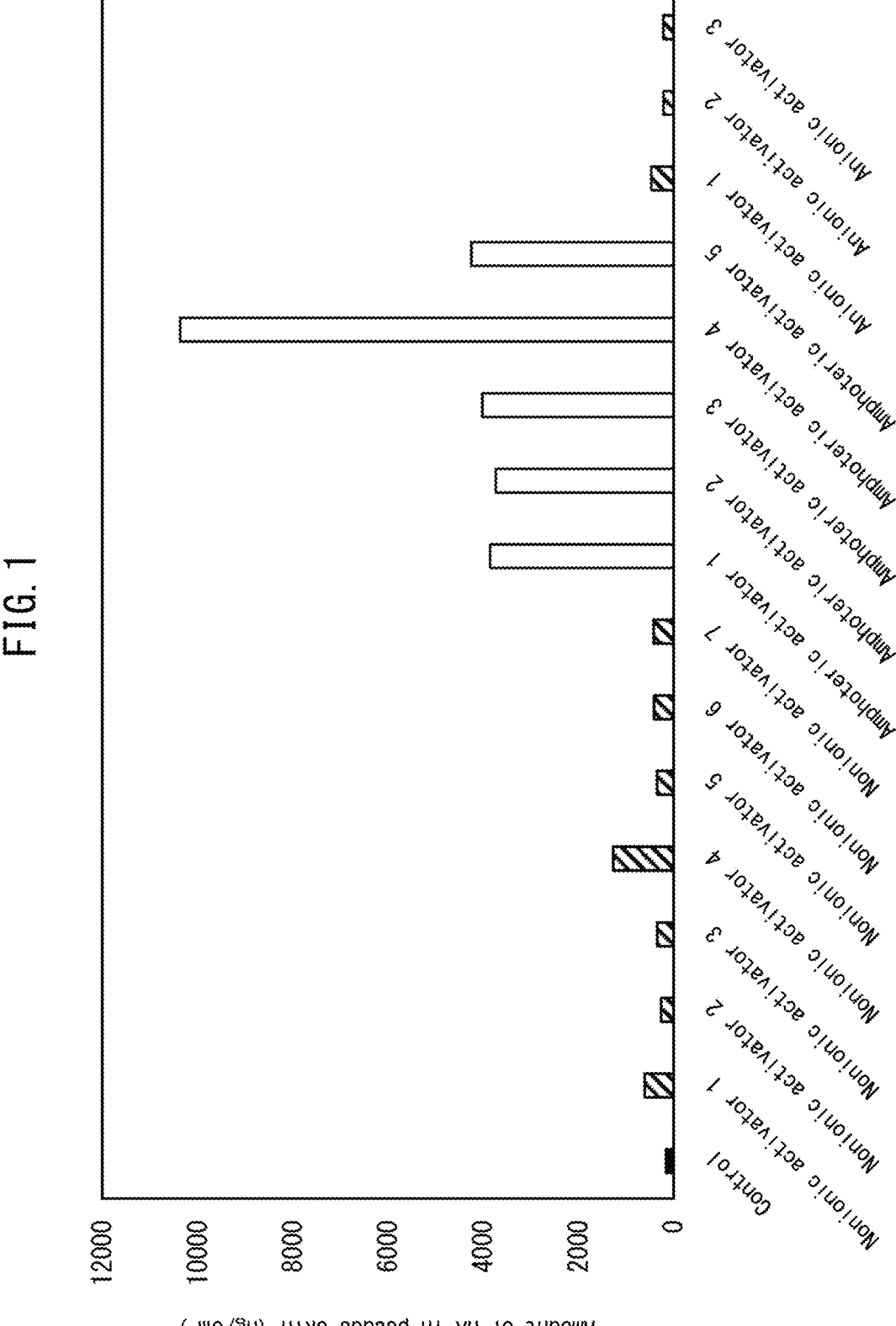
FIG. 1 is a graph related to the amount of a hyaluronate penetrated into a pseudo skin with the use of various surfactants.

As apparent from the results shown in Tables 1 and 2 and FIG. 1, it was confirmed that the penetration of the hyaluronate was improved by incorporating an amphoteric surfactant.

Test Example 2: Effect of Salt Concentration without Amphoteric Surfactant

In Test Example 2, the effect of the salt concentration on the penetration of a hyaluronate when an amphoteric surfactant was not incorporated was examined for reference. The results thereof are shown in FIG. 2.

(Test Sample Preparation Method)

A hyaluronate (manufactured by Shiseido Co., Ltd., BIOHYALURO 12: weight-average molecular weight=1,200,000) was added to ion-exchange water to a content of 0.3% by mass, and the resultant was mixed with stirring using a stirrer to prepare a hyaluronate-containing solution. To each of fractionated portions of this solution, sodium chloride was added at a concentration giving an ionic strength of 0.05, 0.1, 0.2, or 0.5, and the resultant was mixed with stirring, whereby each test sample was prepared.

(Results)

As apparent from the results shown in FIG. 2, it was confirmed that, when an amphoteric surfactant was not contained in the cosmetic, the penetration of the hyaluronate was reduced with the increase in the salt concentration.

Test Example 3: Effect of Salt Concentration with Amphoteric Surfactant

In Test Example 3, the effect of the salt concentration on the penetration of a hyaluronate when an amphoteric surfactant was incorporated was examined. The results thereof are shown in Table 3 and FIG. 3.

Example 2

A test sample of Example 2 of the above-described Test Example 1 was used. The test sample of Example 2 was prepared as follows. A hyaluronate (manufactured by Shiseido Co., Ltd., BIOHYALURO 12: weight-average molecular weight=1,200,000) was added to ion-exchange water to a content of 0.3% by mass, and the resultant was mixed with stirring using a stirrer to prepare a hyaluronate-containing solution. To this solution, lauryl betaine which is an amphoteric surfactant was added to a content of 0.7% by mass, and the resultant was mixed with stirring using a stirrer, whereby the test sample was prepared.

Example 6

Sodium chloride was added to the test sample of Example 2 at a concentration giving an ionic strength of 0.1, and the resultant was mixed with stirring using a vortex mixer, whereby a test sample of Example 6 was prepared.

Example 7

Magnesium chloride was added to the test sample of Example 2 at a concentration giving an ionic strength of 0.21, and the resultant was mixed with stirring using a vortex mixer, whereby a test sample of Example 7 was prepared.

Comparative Example 11

As a test sample of Comparative Example 11, the hyaluronate-containing solution of Example 2, which contained neither an amphoteric surfactant nor a salt, was used.

Comparative Example 12

Sodium chloride was added to the hyaluronate-containing solution of Example 2 at a concentration giving an ionic strength of 0.1, and the resultant was mixed with stirring using a stirrer, whereby a test sample of Comparative Example 12 was prepared.

Comparative Example 13

Magnesium chloride was added to the hyaluronate-containing solution of Example 2 at a concentration giving an ionic strength of 0.21, and the resultant was mixed with stirring using a stirrer, whereby a test sample of Comparative Example 13 was prepared.

TABLE 3

| | Comparative Example 11 | Comparative Example 12 | Comparative Example 13 | Example 2 | Example 6 | Example 7 |
|---|---|---|---|---|---|---|
| Amphoteric surfactant | — | — | — | LB | LB | LB |
| Salt | — | NaCl | MgCl$_2$ | — | NaCl | MgCl$_2$ |
| Penetration Test 1 (ng/cm$^2$) | 155 | 80 | 190 | 3,720 | 3,750 | 1,780 |

(Results)

It was found that, as compared to the cosmetics of Comparative Examples 11 to 13 which did not contain an amphoteric surfactant, the cosmetics of Examples 2, 6, and 7 which contained an amphoteric surfactant improved the penetration of the hyaluronate even when a salt was contained therein.

Test Example 4: Performance on Human Skin

In Test Example 4, the penetration of a hyaluronate into the human skin when an amphoteric surfactant was incorporated was examined. The results thereof are shown in Table 4 and FIG. 4.

Example 8

A hyaluronate (manufactured by Shiseido Co., Ltd., BIOHYALURO 12: weight-average molecular weight=1,200,000) was added to ion-exchange water to a content of 0.5% by mass, and the resultant was mixed with stirring using a stirrer to prepare a hyaluronate-containing solution. To this solution, lauryl betaine which is an amphoteric surfactant was added to a content of 0.1% by mass, and magnesium chloride was further added at a concentration giving an ionic strength of 0.21, after which the resultant was mixed with stirring using a stirrer, whereby a test sample was prepared.

Comparative Example 14

As a test sample of Comparative Example 14, the hyaluronate-containing solution of Example 8, which contained neither an amphoteric surfactant nor a salt, was used.

TABLE 4

| | Comparative Example 14 | Example 8 |
|---|---|---|
| Amphoteric surfactant | — | LB |
| Salt | — | MgCl$_2$ |
| Penetration Test 2 (ng/cm$^2$) | 110 | 610 |

(Results)

It was confirmed that the cosmetic containing the amphoteric surfactant along with the hyaluronate also improved the penetration of the hyaluronate into the human skin.

Test Example 5: Various Moisturizing Agents

In Test Example 5, the effects of various moisturizing agents incorporated together with a hyaluronate and an amphoteric surfactant were examined. The results thereof are shown in Table 5 and FIG. 5. Table 5 shows Comparative Examples 15 to 17, and the results of these Comparative Examples are provided for comparison with the results of Examples 9 to 11. In other words, the test samples of Comparative Examples 15 to 17 also each contained an amphoteric surfactant and exhibited a performance comparable to that of the test sample of Reference Example 2; therefore, the test samples of Comparative Examples 15 to 17 can serve as Examples when compared to a test sample containing no amphoteric surfactant (e.g., the test sample of Comparative Example 1 shown in Table 1).

Comparative Example 15

A hyaluronate (manufactured by Shiseido Co., Ltd., BIOHYALURO 12: weight-average molecular weight=1,200,000) was added to ion-exchange water to a content of 0.3% by mass, and the resultant was mixed with stirring using a stirrer to prepare a hyaluronate-containing solution. To this solution, lauryl betaine which is an amphoteric surfactant was added to a content of 0.7% by mass, and glycerol which is a moisturizing agent was added to a content of 10% by mass, after which sodium chloride was further added at a concentration giving an ionic strength of 0.1, and the resultant was mixed with stirring using a stirrer, whereby a test sample was prepared.

Examples 9 to 11 and Comparative Examples 16 and 17

Test samples of Examples 9 to 11 and Comparative Examples 16 and 17 were each prepared in the same manner as in Comparative Example 15, except that the moisturizing agent was changed as shown in Table 5.

Reference Example 2

A test sample of Reference Example 2 (control sample) was prepared in the same manner as in Comparative Example 15, except that the moisturizing agent was not used.

TABLE 5

| | Reference Example 2 | Comparative Example 15 | Example 9 | Comparative Example 16 | Example 10 | Comparative Example 17 | Example 11 |
|---|---|---|---|---|---|---|---|
| Amphoteric surfactant | | | | lauryl betaine (LB) | | | |
| Salt | | | | NaCl | | | |
| Moisturizing agent | — | glycerol | propylene glycol (PG) | butylene glycol (BG) | dipropylene glycol (DPG) | ethanol | PEG/PPG-17/4 dimethyl ether |
| Penetration Test 1 (ng/cm$^2$) | 3,750 | 3,600 | 7,890 | 3,600 | 6,080 | 3,460 | 6,710 |

(Results)

It was found that, in those cases where propylene glycol, dipropylene glycol, or PEG/PPG-17/4 dimethyl ether was used as a moisturizing agent, the penetration of the hyaluronate was further improved as compared to the cosmetic containing no such a moisturizing agent and the cosmetic containing other moisturizing agent.

Test Example 6: Synergistic Effect Associated with Use of Moisturizing Agent or Moisturizing Agent and Salt in Combination with Amphoteric Surfactant In Test Example 6, the synergistic effect associated with the use of a moisturizing agent, or a moisturizing agent and a salt, in combination with an amphoteric surfactant was examined. The results thereof are shown in Table 6 and FIG. 6. Table 6 and FIG. 6 also provide the results of the above-described Comparative Examples 11 and 13. It is noted here that the results of the penetration test 1 of Comparative Examples 11 and 13 were obtained at 24 hours after the application of each cosmetic to the donor section in an amount of 10 µL/cm$^2$, while the results of the penetration test 1 of Reference Example 3 and Examples 12 to 14 were obtained at 6 hours after the application of each cosmetic to the donor section in an amount of 10 µL/cm$^2$.

Example 12

A hyaluronate (manufactured by Shiseido Co., Ltd., BIOHYALURO 12: weight-average molecular weight=1,200,000) was added to ion-exchange water to a content of 0.3% by mass, and the resultant was mixed with stirring using a stirrer to prepare a hyaluronate-containing solution. To this solution, lauryl betaine which is an amphoteric surfactant was added to a content of 0.1% by mass, and dipropylene glycol which is a moisturizing agent was added to a content of 9% by mass, after which the resultant was mixed with stirring using a vortex mixer, whereby a test sample was prepared.

Example 13

A hyaluronate (manufactured by Shiseido Co., Ltd., BIOHYALURO 12: weight-average molecular weight=1,200,000) was added to ion-exchange water to a content of 0.3% by mass, and the resultant was mixed with stirring using a stirrer to prepare a hyaluronate-containing solution. To this solution, lauryl betaine which is an amphoteric surfactant was added to a content of 0.1% by mass, and dipropylene glycol which is a moisturizing agent was added to a content of 9% by mass, after which magnesium chloride was further added at a concentration giving an ionic strength of 0.21, and the resultant was mixed with stirring using a vortex mixer, whereby a test sample was prepared.

Example 14

A test sample of Example 14 was prepared in the same manner as in Example 13, except that sodium chloride was added in place of magnesium chloride at a concentration giving an ionic strength of 0.1.

Reference Example 3

A test sample of Reference Example 3 was prepared in the same manner as in Example 12, except that the moisturizing agent was not used.

TABLE 6

| | Comparative Example 11 | Comparative Example 13 | Reference Example 3 | Example 12 | Example 13 | Example 14 |
|---|---|---|---|---|---|---|
| Amphoteric surfactant | — | — | LB | LB | LB | LB |
| Salt | — | MgCl$_2$ | — | — | MgCl$_2$ | NaCl |
| Moisturizing agent | — | — | — | DPG | DPG | DPG |
| Penetration Test 1 (ng/cm$^2$) | 155 | 190 | 1,570 | 2,380 | 3,110 | 4,740 |

(Results)

As apparent from a comparison of Reference Example 3 and Example 12, it was found that the penetration of the hyaluronate was improved by using dipropylene glycol, which is a moisturizing agent, in combination with the amphoteric surfactant.

It was also found that the penetration of the hyaluronate was further improved by using a salt, particularly sodium chloride, in addition to dipropylene glycol. This salt addition effect is expected to be exerted in the same manner also for other moisturizing agents (propylene glycol and PEG/PPG-17/4 dimethyl ether) that improved the penetration of the hyaluronate when used in combination with an amphoteric surfactant.

The invention claimed is:

1. A hyaluronate skin-penetrating cosmetic, comprising a hyaluronate and an amphoteric surfactant,
wherein the weight-average molecular weight of the hyaluronate is 300,000 or more, and wherein the hyaluronate does not contain hyaluronate derivatives, and
wherein the amphoteric surfactant comprises at least one selected from the group consisting of betaine-type amphoteric surfactants, amino acid-type amphoteric surfactants, sulfonic acid-type amphoteric surfactants, sulfate-type amphoteric surfactants, and lecithin.

2. The cosmetic according to claim 1, comprising a salt at a concentration giving an ionic strength of 0.05 or more.

3. The cosmetic according to claim 1, wherein the content of the amphoteric surfactant is 0.01% by mass or more with respect to a total amount of the cosmetic.

4. The cosmetic according to claim 2, wherein the salt is at least one selected from the group consisting of monovalent salts, divalent salts, and trivalent salts.

5. The cosmetic according to claim 2, wherein the salt is at least one selected from the group consisting of a sodium salt and a magnesium salt.

6. The cosmetic according to claim 5, wherein the sodium salt is sodium chloride, and the magnesium salt is magnesium chloride.

7. The cosmetic according to claim 1, comprising at least one moisturizing agent selected from the group consisting of propylene glycol, dipropylene glycol, and PEG/PPG-17/4 dimethyl ether.

8. The cosmetic according to claim 7, comprising sodium chloride.

9. The cosmetic according to claim 1, wherein the amphoteric surfactant comprises lecithin.

* * * * *